US009730686B2

(12) United States Patent
Ampuero et al.

(10) Patent No.: US 9,730,686 B2
(45) Date of Patent: Aug. 15, 2017

(54) SYSTEM AND METHOD OF SOFT TISSUE ANCHORING TO METAPHYSEAL BONE PLATE

(71) Applicant: Biomet C.V., Gibraltar (GI)

(72) Inventors: Eduardo A. Ampuero, Miami, FL (US); Alfredo Castaneda, Miami, FL (US); Joel G. Marquart, Pembroke Pines, FL (US)

(73) Assignee: Biomet C.V., Warsaw, IN (US)

( * ) Notice: Subject to any disclaimer, the term of this patent is extended or adjusted under 35 U.S.C. 154(b) by 195 days.

(21) Appl. No.: 14/476,475

(22) Filed: Sep. 3, 2014

(65) Prior Publication Data

US 2016/0058486 A1   Mar. 3, 2016

(51) Int. Cl.
| | | |
|---|---|---|
| *A61B 17/80* | (2006.01) | |
| *A61B 17/04* | (2006.01) | |
| *A61B 17/56* | (2006.01) | |
| *A61B 17/06* | (2006.01) | |

(52) U.S. Cl.
CPC ...... *A61B 17/0401* (2013.01); *A61B 17/8061* (2013.01); *A61B 17/8085* (2013.01); *A61B 17/8057* (2013.01); *A61B 2017/0408* (2013.01); *A61B 2017/06052* (2013.01); *A61B 2017/06057* (2013.01); *A61B 2017/564* (2013.01)

(58) Field of Classification Search
CPC ............ A61B 17/8085; A61B 17/8061; A61B 17/842; A61B 17/82; A61B 17/0401
See application file for complete search history.

(56) References Cited

U.S. PATENT DOCUMENTS

| | | | |
|---|---|---|---|
| 3,741,205 | A | 6/1973 | Markolf et al. |
| 3,842,825 | A | 10/1974 | Wagner |
| 4,219,015 | A | 8/1980 | Steinemann |

(Continued)

FOREIGN PATENT DOCUMENTS

| | | |
|---|---|---|
| DE | 8628766 | 12/1986 |
| EP | 0206767 | 12/1986 |

(Continued)

OTHER PUBLICATIONS

"International Application Serial No. PCT/IB2015/001923, International Search Report mailed Jul. 14, 2016", 4 pgs.

(Continued)

*Primary Examiner* — David Bates
*Assistant Examiner* — Olivia C Chang
(74) *Attorney, Agent, or Firm* — Schwegman Lundberg & Woessner, P.A.

(57) ABSTRACT

A bone plate a re-orientable tab that provides a buttress support to fragments of the surrounding concave joint rim. The tabs can be re-orientated to contact the rim to provide close support. Each tab includes a hole sized to closely receive a K-wire to permit the K-wire to apply a bending load to a tab in situ to bend the tab about a lower recess between the tab and the remainder of the head. A soft tissue anchor is sized to pass through the hole in the tab, and into a hole drilled into the underlying bone. The soft tissue anchor has a bone engaging first portion and second portion comprising a length of flexible suture, to which is affixed a needle. The needle and suture can be used to draw tissue about the joint capsule.

20 Claims, 3 Drawing Sheets

(56) References Cited

U.S. PATENT DOCUMENTS

| | | | |
|---|---|---|---|
| 4,388,921 | A | 6/1983 | Sutter et al. |
| 4,573,458 | A | 3/1986 | Lower |
| 4,955,886 | A | 9/1990 | Pawluk |
| 4,973,332 | A | 11/1990 | Kummer |
| 5,057,109 | A | 10/1991 | Olerud |
| 5,147,361 | A | 9/1992 | Ojima et al. |
| 5,616,144 | A | 4/1997 | Yapp et al. |
| 5,647,712 | A | 7/1997 | Demirdogen et al. |
| 5,772,662 | A | 6/1998 | Chapman et al. |
| 5,954,722 | A | 9/1999 | Bono |
| 6,004,353 | A | 12/1999 | Masini |
| 6,123,709 | A | 9/2000 | Jones |
| 6,206,881 | B1 | 3/2001 | Frigg et al. |
| 6,364,882 | B1 | 4/2002 | Orbay |
| 6,454,769 | B2 | 9/2002 | Wagner et al. |
| 6,506,191 | B1 | 1/2003 | Joos |
| 6,565,570 | B2 | 5/2003 | Sterett et al. |
| 6,623,486 | B1 | 9/2003 | Weaver et al. |
| 6,652,530 | B2 | 11/2003 | Ip et al. |
| 6,712,820 | B2 | 3/2004 | Orbay |
| 6,786,909 | B1 | 9/2004 | Dransfeld et al. |
| 6,866,665 | B2 | 3/2005 | Orbay |
| 7,189,237 | B2 | 3/2007 | Huebner |
| 7,250,053 | B2 | 7/2007 | Orbay |
| 7,294,130 | B2 | 11/2007 | Orbay |
| 7,335,204 | B2 | 2/2008 | Tornier |
| 7,604,657 | B2 | 10/2009 | Orbay et al. |
| 7,818,542 | B2 | 10/2010 | Shen et al. |
| 7,935,126 | B2 | 5/2011 | Orbay et al. |
| 7,951,176 | B2 | 5/2011 | Grady, Jr. et al. |
| 8,021,402 | B2 | 9/2011 | Martin et al. |
| 8,469,999 | B2 | 6/2013 | Gonzalez-Hernandez |
| 8,562,647 | B2 | 10/2013 | Kaiser et al. |
| 8,632,574 | B2 | 1/2014 | Kortenbach et al. |
| 8,790,378 | B2 | 7/2014 | Castaneda et al. |
| 9,510,881 | B2 | 12/2016 | Castaneda et al. |
| 2004/0210220 | A1 | 10/2004 | Tornier |
| 2005/0085818 | A1 | 4/2005 | Huebner |
| 2005/0234458 | A1 | 10/2005 | Huebner |
| 2007/0093837 | A1 | 4/2007 | Bohrmann et al. |
| 2007/0233111 | A1 | 10/2007 | Orbay |
| 2007/0270849 | A1* | 11/2007 | Orbay ............... A61B 17/74 606/291 |
| 2008/0140127 | A1 | 6/2008 | Vasta et al. |
| 2009/0018587 | A1 | 1/2009 | Bottlang |
| 2009/0118769 | A1* | 5/2009 | Sixto, Jr. ............ A61B 17/8061 606/280 |
| 2009/0143825 | A1 | 6/2009 | Graham |
| 2009/0275987 | A1 | 11/2009 | Graham et al. |
| 2010/0057086 | A1 | 3/2010 | Price et al. |
| 2010/0262185 | A1* | 10/2010 | Gelfand ............ A61B 17/0401 606/232 |
| 2011/0118795 | A1 | 5/2011 | Hashmi et al. |
| 2013/0079828 | A1 | 3/2013 | Glickel |
| 2013/0172944 | A1* | 7/2013 | Fritzinger .......... A61B 17/0401 606/286 |
| 2013/0204307 | A1* | 8/2013 | Castaneda ......... A61B 17/8061 606/297 |
| 2014/0067081 | A1 | 3/2014 | Stone |
| 2014/0128921 | A1 | 5/2014 | Parsons et al. |
| 2014/0214089 | A1 | 7/2014 | Glickel |
| 2014/0330321 | A1 | 11/2014 | Castaneda et al. |

FOREIGN PATENT DOCUMENTS

| | | |
|---|---|---|
| EP | 2809251 B1 | 2/2017 |
| FR | 742618 | 3/1933 |
| GB | 2477086 | 7/2011 |
| WO | WO 89/04150 | 5/1989 |
| WO | WO 97/09000 | 3/1997 |
| WO | WO 01/30251 | 5/2001 |
| WO | WO-2013115911 A1 | 8/2013 |
| WO | WO-2013204307 A1 | 8/2013 |
| WO | WO-2016038456 A2 | 3/2016 |
| WO | WO-2016038456 A3 | 3/2016 |

OTHER PUBLICATIONS

"International Application Serial No. PCT/IB2015/001923, Invitation to Pay Additional Fees and Partial Search Report mailed May 9, 2016", 3 pgs.

"International Application Serial No. PCT/IB2015/001923, Written Opinion maiiad Jul. 14, 2016", 6 pgs.

2.4 mm Variable Angle LCP Distal Radius System. For fragment-specific fracture fixation with variable angle locking technology. Technique Guide, Synthes, 2008.

JuggerKnot™ Soft Anchor, All-Inclusive Brochure; Form No. BMET0696.1; Rev 0114; pp. 1-24; Biomet Sports Medicine 2014.

JuggerKnot™ Soft Anchor; Form No. BSM0285.0; Rev 061511; pp. 1-2; Biomet Sports Medicine 2011.

Matsuda, Dean, MD et al; JuggerKnot Long Soft Anchor for Hip Acetabular Labral Repair; Form No. BMET0211.0-GBL; Rev 0514; pp. 1-16; Biomet Sports Medicine 2014.

"U.S. Appl. No. 13/364,513, Non Final Office Action mailed Sep. 11, 2013", 8 pgs.

"U.S. Appl. No. 13/364,513, Non Final Office Action mailed Dec. 9, 2013", 9 pgs.

"U.S. Appl. No. 13/364,513, Notice of Allowance mailed Mar. 28, 2014", 5 pgs.

"U.S. Appl. No. 13/364,513, Response filed Feb. 28, 2014 to Non Final Office Action mailed Dec. 9, 2013", 20 pgs.

"U.S. Appl. No. 13/364,513, Response filed Oct. 9, 2013 to Non Final Office Action mailed Sep. 11, 2013", 17 pgs.

"U.S. Appl. No. 14/291,113, Non Final Office Action mailed Mar. 8, 2016", 10 pgs.

"U.S. Appl. No. 14/291,113, Notice of Allowance mailed Aug. 3, 2016", 7 pgs.

"U.S. Appl. No. 14/291,113, Response filed Jul. 7, 2016 to Non Final Office Action mailed Mar. 8, 2016", 16 pgs.

"U.S. Appl. No. 15/357,521, Preliminary Amendment filed Feb. 1, 2017", 7 pgs.

"European Application Serial No. 12816809.3, Communication pursuant to Article 94(3) ,EPC mailed Aug. 25, 2015", 6 pgs.

"European Application Serial No. 12816809.3, Office Action mailed Sep. 11, 2014", 2 pgs.

"European Application Serial No. 12816809.3, Response filed Mar. 5, 2015 to Office Action mailed Sep. 11, 2014", 13 pgs.

"International Application Serial No. PCT/US2012/069342, International Preliminary Report on Patentability mailed Aug. 14, 2014", 8 pgs.

"International Application Serial No. PCT/US2012/069342, International Search Report mailed Feb. 22, 2013", 4 pgs.

"International Application Serial No. PCT/US2012/069342, Written Opinion mailed Feb. 22, 2013", 6 pgs.

* cited by examiner

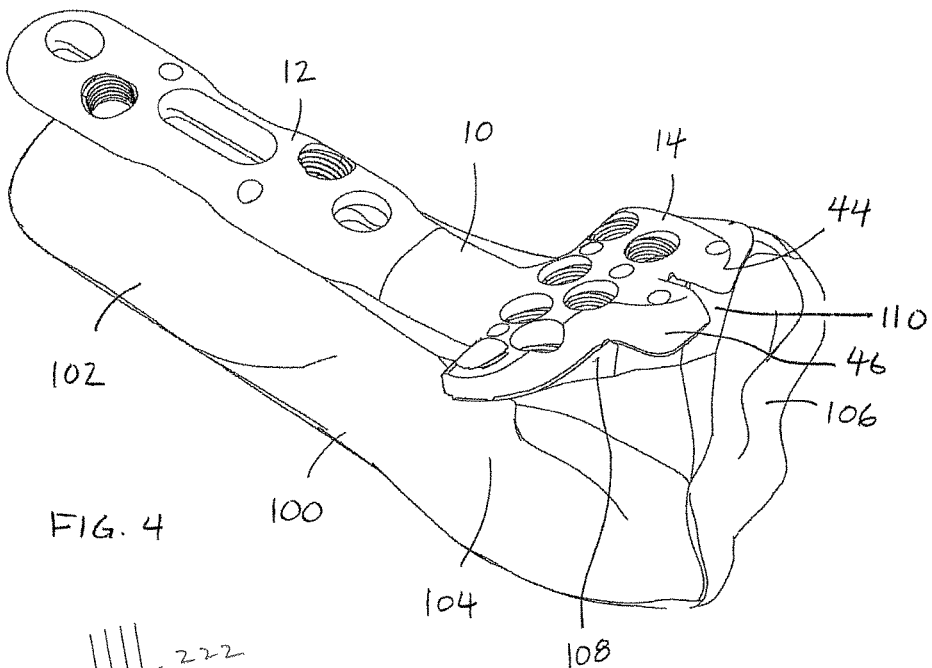
FIG. 4
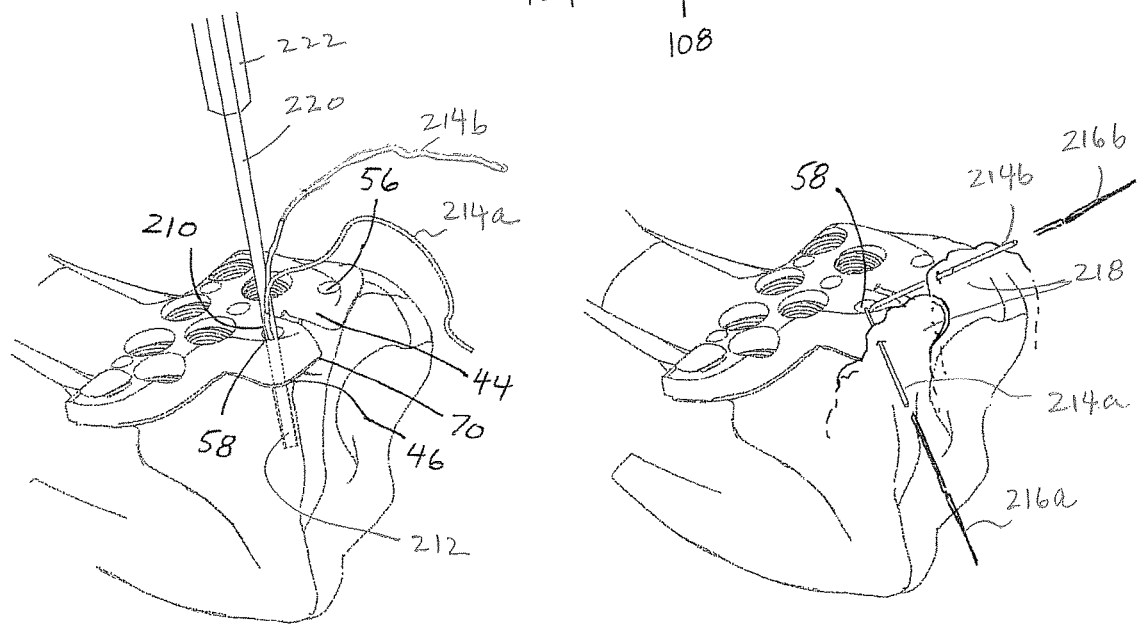
FIG. 10
FIG. 11

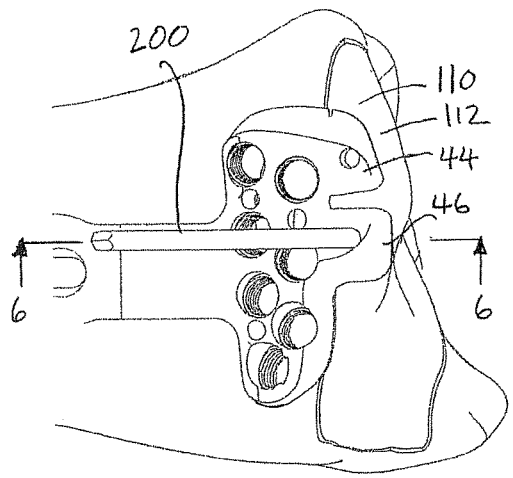
FIG. 5
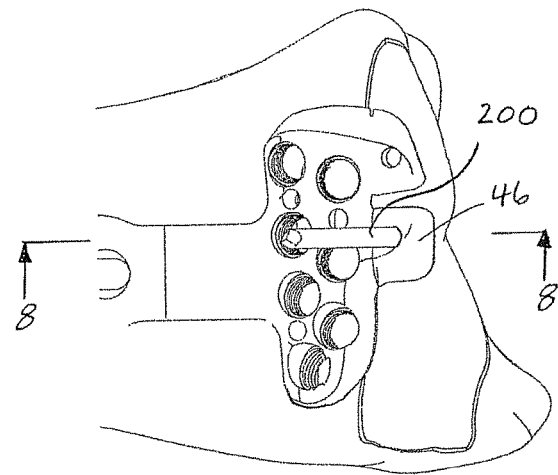
FIG. 7
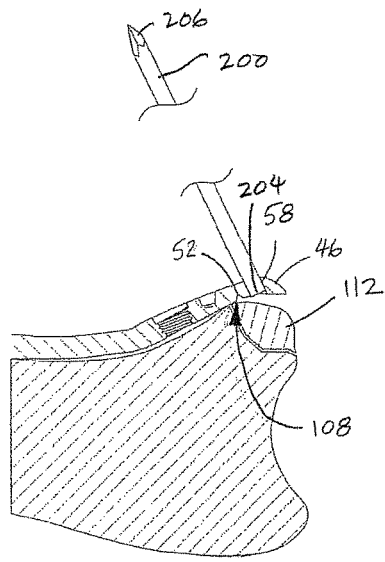
FIG. 6
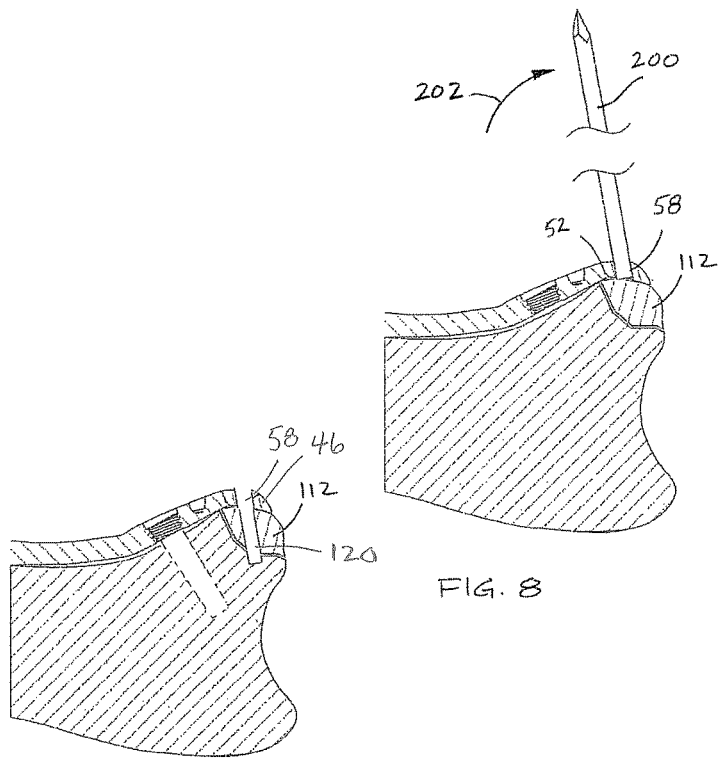
FIG. 8
FIG. 9

SYSTEM AND METHOD OF SOFT TISSUE ANCHORING TO METAPHYSEAL BONE PLATE

BACKGROUND OF THE INVENTION

1. Field of the Invention

This invention relates broadly to surgical implants. More particularly, this invention relates to bone fracture and soft tissue fixation systems for use at a metaphysis.

2. State of the Art

Fracture to the metaphyseal portion of a long bone can be difficult to treat. Improper treatment can result in deformity and long-term discomfort.

By way of example, a Barton's fracture represents a fracture dislocation or subluxation of the wrist in which the dorsal or volar rim of the distal radius is displaced relative to the carpal bones. However, volar involvement is more common. As another example, a Colles' fracture is a fracture resulting from compressive forces being placed on the distal radius, and which causes backward or dorsal displacement of the distal fragment and radial deviation of the hand at the wrist. Often, a Colles' fracture will result in multiple bone fragments which are movable and out of alignment relative to each other. If these fractures are not properly treated, permanent wrist deformity may result, as well as limited articulation of the wrist. It is therefore important to align the fracture and fixate the bones relative to each other so that proper healing may occur.

Alignment and fixation of a metaphyseal fracture (occurring at the extremity of a shaft of a long bone) are typically performed by one of several methods: casting, external fixation, pinning, and plating. Casting is non-invasive, but may not be able to maintain alignment of the fracture where many bone fragments exist. Therefore, as an alternative, external fixators may be used. External fixators utilize a method known as ligamentotaxis, which provides distraction forces across the joint and permits the fracture to be aligned based upon the tension placed on the surrounding ligaments. However, while external fixators can maintain the position of the wrist bones, it may nevertheless be difficult in certain fractures to first provide the bones in proper alignment. In addition, external fixators are often not suitable for fractures resulting in multiple bone fragments. Pinning with K-wires (Kirschner wires) is an invasive procedure whereby pins are positioned into the various fragments. This is a difficult and time consuming procedure that provides limited fixation if the bone is comminuted or osteoporotic. Plating utilizes a stabilizing metal plate typically placed against the side of a bone, and screws extending from the plate into holes drilled in the bone fragments to provide stabilized fixation of the fragments. However, many currently available plate systems fail to provide desirable alignment and stabilization.

The distal radius exhibits a concave shape extending from the shaft, which reaches an inflection point at a so-called watershed line followed by a convex like form at its most prominent feature, the volar rim. With a distal radius fracture, the complex shape of the distal radius, including the prominent volar rim of the lunate fossa, relatively flat volar rim of the scaphoid fossa, and the sometimes prominent base of the styloid process should be accommodated. Furthermore, the ligaments extending from the volar side of the distal radius to the intercarpal bones must not be irritated or distressed. Moreover, a fixation device should provide desirable alignment and stabilization of the bone structure proximate the articular surface of the distal radius.

Co-owned U.S. Pat. No. 7,250,053 to Orbay discloses a volar plate for the distal radius that accommodates the anatomy. The plate includes a head for placement at the metaphysis and a shaft for extension along the diaphysis. The head and shaft each include holes for receiving fasteners to couple the plate to the bone. The holes in the head are threaded fixed angle holes oriented to extend the shaft of the fasteners in a spatial distribution through the bone about the articular surface to provide significant support and early mobility. In addition, the top portions of the plate are such that they provide a buttress support for the fragment while providing a smooth contour to minimize soft tissue interaction and not creating a prominent sharp edge nearest the inflexion point or 'watershed line' of the volar rim. This is achieved by a contoured shape that blends back into the anatomy without extending into the articular surface. The lower surface of the ulnar side of the head of this plate is contoured to accommodate the concave shape of the distal radius below the watershed line. It is specifically indicated that the watershed line is not to be violated by the plate.

However, volar ulnar facet fractures occur in the distal portion of the concave form of the distal radius and require additional fixation. The fractures may involve displaced avulsions, shear fractures and small fragments that are in the vicinity of the prominent portion of the volar rim. These fractures are difficult to treat with existing hardware since most available hardware could interfere with surrounding soft tissue and/or increase the likelihood impinging on the articular surfaces of the distal radius.

U.S. Pub. No. 20090275987 to Graham proposes various plates and adjunct extenders that can be physically attached to the plates with screws to provide supplementary anatomical support. The extenders are not ideally shaped to limit interference with soft tissue. In addition, this type of support requires the attachment of very small plates to the primary plate and can be difficult to work with, particularly in the operating room and during a surgical procedure. There is no easy and reliable way to fit the extenders to the anatomy during the procedure.

Co-owned U.S. Pub. No. 20130204307 to Castaneda describes a volar rim plate that includes integrated tabs that extend over the volar ulnar facet to provide a buttress support thereover. The tabs can be readily re-orientated to approximate the volar rim and provide close support. In order to re-orient the tabs, the tabs are provided with a respective lower recess, that allows each tab to be contoured independently to fit the patient anatomy. Each tab is provided with a hole sized to closely receive a K-wire that permits the K-wire to apply a bending load to a tab in situ to bend the tab about its lower recess into a new orientation to best match the patient anatomy and provide support. Therefore, the plate does not require a dedicated bender. In addition, the hole in each tab is spaced relative to the distal peripheral edge of the tab to accommodate passage of a suture needle completely therethrough. With the tab slightly spaced from the volar rim, the suture needle can be passed through the gap between the tab and the volar rim and then through soft tissue to join the soft tissue to the plate; i.e., to facilitate repair of the joint capsule. However, such repair can result in the tab being slightly displaced from the volar rim, which may not be ideal.

SUMMARY OF THE INVENTION

A metaphyseal plate is provided having a shaft for placement on the diaphysis of a long bone, such as a radius bone, and a head angled relative to the shaft and shaped for low profile placement on the metaphysis of the long bone. The plate has a lower bone contacting surface and an opposite upper surface. The head and shaft each include holes for receiving fasteners to couple the plate to the bone. The holes in the head are preferably threaded, fixed angle holes. The holes are oriented to extend screws in a spatial distribution through the bone and about the articular surface of the metaphysis to provide significant support.

The plate is provided with two smoothly contoured and chamfered distally extending tabs for extension over and beyond an inflexion line of a boney crest when the plate is positioned on the bone. In a distal volar plate, the tabs provide a buttress support over the volar ulnar facet. The tabs each have a smoothly contoured upper surface that is adapted to be atraumatic to the soft tissue and thereby minimize soft tissue irritation. In addition, the tabs can be readily re-orientated to rest directly on bone fragments to provide close support. This keeps the fragments very stable. In order to re-orient the tabs, the tabs are each provided with respective lower recesses, preferably as an undercut at the junction of the tabs and the remainder of the head plate. In an embodiment of the plate, from the lower surface of the plate, the undercut and distal edge of the lateral side of the plate are in alignment. The recesses allow each tab to be contoured independently to fit the patient anatomy. Each tab is provided with preferably a single hole sized to closely receive a K-wire in a fixed angle orientation. This permits a K-wire to apply a bending load to a tab in situ to bend the tab about its lower recess into a new orientation to best match the patient anatomy and provide support. Therefore, the plate does not require a dedicated bender.

A soft tissue anchor is also provided that can be used to join soft tissue relative to the hole in the tab of the plate. The soft tissue has a first portion that engages bone and a second suture portion terminating in a needle that can be inserted through soft tissue. The first portion of the soft tissue anchor is specifically adapted to pass directly through the hole in the tab and into the underlying bone to anchor the soft tissue relative to the tab and bone, whereas the second suture portion is adapted to engage capsular tissue and retain it relative to the plate.

In use, the plate is positioned on the bone with the primary terminating edge of the plate located below the boney crest inflexion line on the bone, with the tabs providing buttress support for the bone beyond the inflexion line. Fixation is provided between the plate and the diaphyseal portion of the bone by inserting fasteners through the screw holes in the shaft and head of the plate and into the underlying bone. To the extent necessary or desired, the tabs are bent along the recessed to rest directly on the bone. A hole is drilled through a hole in a tab and into the underlying the bone. The first portion of the soft tissue anchor is inserted through the hole in the tab and into the hole in the underlying bone, and the second portion is then engaged relative to soft tissue which is secured in position relative to the plate and bone.

The system and method permit sutures to be applied after the plate has been fully installed, even when the plate is in contact with the underlying bone. This makes the process intuitive, allowing the surgeon to focus on reducing the fracture and correctly securing the plate to the bone prior to addressing the stability of soft tissue. In addition, the system and procedure allow the plate to be secured in close contact, and thus a more stable positioning, relative to the bone.

BRIEF DESCRIPTION OF THE DRAWINGS

FIG. 4 is a perspective view of the plate of FIG. 1 shown on a portion of a distal radius bone.

FIG. 5 is a top view and a FIG. 6 is a longitudinal section view along line 6-6 in FIG. 5, both illustrating insertion of a K-wire into a hole in an extension tab of the distal radius plate prior to bending of the tab.

FIG. 7 is a top view and a FIG. 8 is a longitudinal section view along line 8-8 in FIG. 7, both illustrating use of a K-wire to bending the extension tab of the distal radius plate onto the bone, with the K-wire inserted into the hole in the extension tab.

FIG. 9 is a longitudinal section view similar to FIG. 8, showing a hole drilled through the hole in an extension tab.

FIG. 10 is a perspective views illustrating implantation of a suture anchor through the hole in the extension tab and into the drilled hole.

FIG. 11 is a perspective views illustrating a suture portion of the suture anchor being used to secure soft tissue at the joint capsule.

DETAILED DESCRIPTION OF THE PREFERRED EMBODIMENTS

Figure 1:
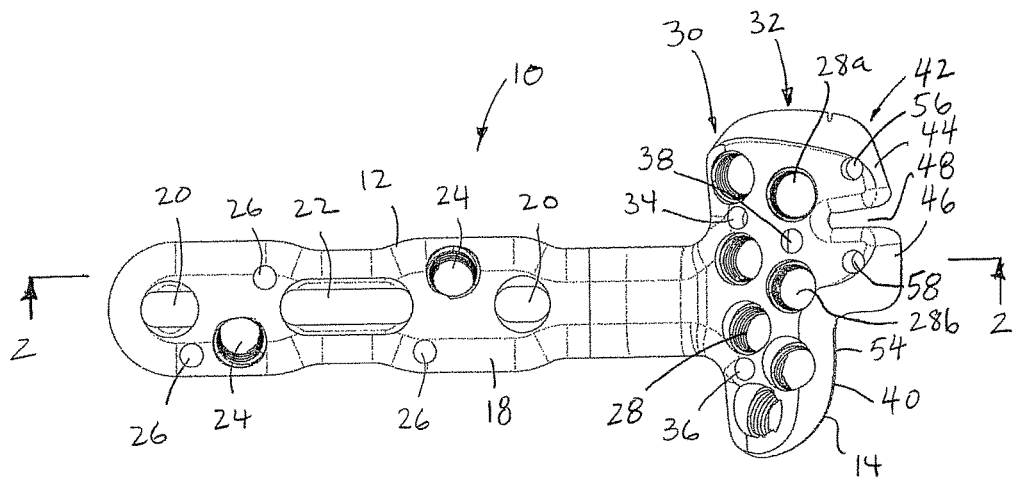
FIG. 1 is a top view of a distal radius plate according to a prior art the invention.

Turning now to FIGS. 1 through 4, a bone plate 10 for stabilization of a fracture of a distal radius bone 100 is shown. The plate 10 includes a shaft 12 for placement on the diaphysis 102 of a long bone, such as the distal radius bone 100, and a wider head 14, for example extending in a transverse orientation relative to the shaft, for placement on the metaphysis 104 of the long bone. The plate includes a bone contacting lower surface 16 and an opposite upper surface 18. The head is in angled upward relative to the shaft when the lower surface 16 of the shaft is positioned substantially horizontal and face down in contact with the diaphysis of the long bone.

The shaft 12 and head 14 each include holes for receiving fasteners to couple the plate 10 to the bone 100. The shaft 12 preferably includes a combination of compression holes 20, 22 and non-compression fixed angle, threaded holes 24. The compression holes preferably comprise both circular holes 20 and elongate slots 22. Preferably, the holes 20, 22, 24 comprise the system of holes described in co-owned and co-pending U.S. Pat. No. 8,632,574, which is hereby incorporated by reference herein in its entirety. Holes of another design for suitable fasteners may also be used; however, it is preferable that any provided holes and arrangement thereof include both circular holes and slots, and that such circular holes include a combination of compression holes for compression fasteners and fixed angled holes such as can accommodate a fastener with a threaded head in a fixed orientation. The plate may also include one of more K-wire holes 26 to closely receive respective K-wires for temporary fixation of the shaft 12 of the plate relative to the bone 100.

The holes 28 in the head of the plate 14 are preferably threaded, fixed angle holes, with the threads of each hole defining a respective fixed axis for a fastener inserted therethrough. In a preferred embodiment, the threaded holes 28 are preferably of a same configuration and size as the threaded holes 24, and thus capable of receiving and fixing a common fastener therewith. One exemplar fastener 150 is shown in phantom in FIG. 2. The holes 28 are preferably arranged in two rows; a relatively proximal row 30 and a relatively distal row 32, the rows 30, 32 being acutely angled relative to each other. In a preferred embodiment, the proximal row 30 of holes includes preferably four threaded holes 28, and the distal row 32 includes two or three threaded holes 28 preferably arranged in an offset or interleaving manner from the proximal row 30 such that the shafts of fasteners inserted in the proximal row 30 can extend distally between the shafts of the fasteners inserted in the distal row 32 in an interleaved manner. More preferably, when the plate is positioned on the bone at the intended location, the fasteners 150 extend into the bone in a spatial distribution about the articular surface 106 (FIG. 4) of the wrist socket to provide subchondral support. All the threaded fixed angle holes 28 within the head 14 of the plate are provided to be located in the subchondral bone below an inflexion point on the metaphysis of the bone. In a distal radius bone, this inflexion point on the volar side of the bone is commonly referred to as the watershed line (seen also in FIG. 6). Preferred locations of the threaded holes 28 relative to the volar distal radius and preferred axial orientations of such threaded holes are described in detail in U.S. Pat. No. 7,294,130, which is hereby incorporated by reference herein in its entirety.

K-wire holes are also preferably provided relative to the threaded holes in the head of the plate. A K-wire hole 34 is provided between two adjacent holes in the proximal row 30 of threaded holes, and another K-wire hole 38 is provided between two adjacent holes in the distal row 32 of threaded holes. The K-wire holes 34, 36 are sized to closely receive a K-wire such that an appropriately sized K-wire inserted therethrough is retained at a fixed angle relative to the plate 10 by the sidewalls of the respective K-wire hole. Such holes can be used for temporary fixation of the plate to the bone. Further, the K-wire, whether or not providing such temporary fixation, can be examined under fluoroscopy to analyze its trajectory relative to the bone anatomy and thereby provide information with respect to the apparent trajectory of fasteners through the adjacent threaded holes. In this manner, the K-wires inserted through the K-wire holes provided feedback as to the appropriate placement of the plate prior to drilling larger holes in the bone for the relatively larger fasteners. Additional small K-wire-sized holes can be provided to the head of the plate for purposes of determining adjacent hole alignment, temporary fixation, or as anchor holes for suture to secure bone fragments and soft tissue relative to the plate, as described in more detail hereinafter.

Figure 2:
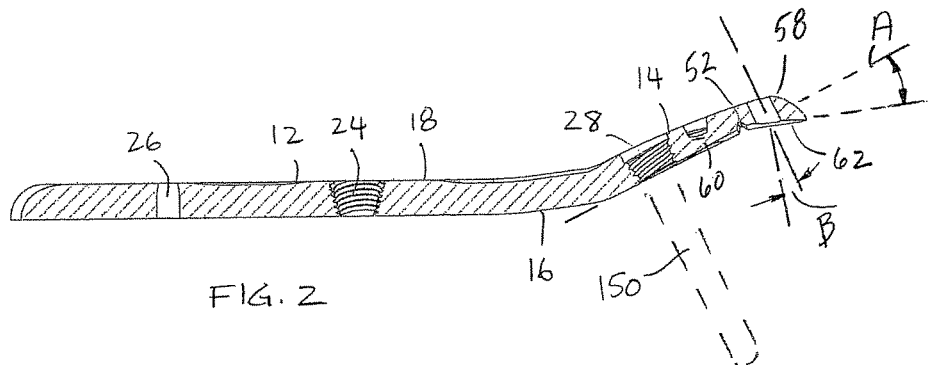
FIG. 2 is a longitudinal section view along line 2-2 in FIG. 1.
Figure 3:
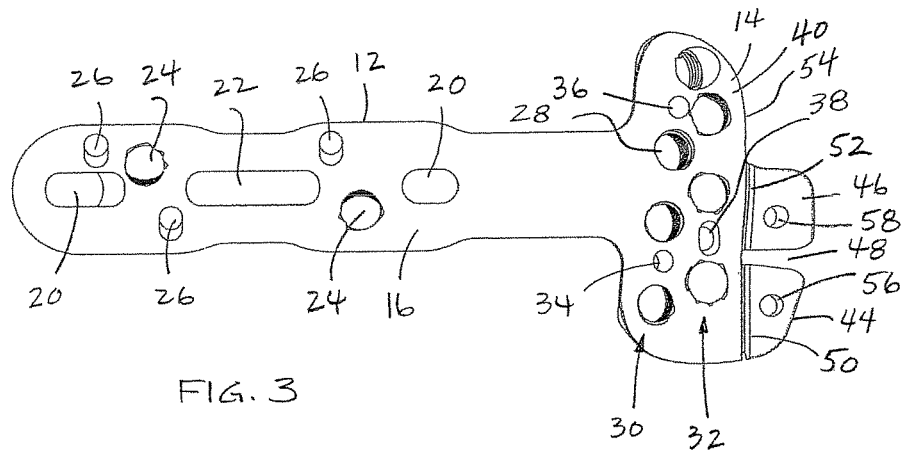
FIG. 3 is a bottom view of the plate of FIG. 1.

Referring to FIGS. 1 and 3, the radial side 40 of the plate 10 is tapered to a distal edge 54 and sized and shaped to seat completely below the boney crest inflexion line 108 on the metaphysis. In distinction, the ulnar (i.e., medial) side 42 of the distal edge of the plate is provided with two distally extending tabs 44, 46 separated from each other by a space 48. As shown, the radial side 40 is free and absent of any such tabs. While the tabs 44, 46 extend from the ulnar (i.e., medial) side 42 of the distal edge, the tabs do not extend the lateral dimension of the head of the plate; the entire extension is preferably distal and displaced to the ulnar side. The tabs 44, 46 extend approximately 5 mm beyond the distal edge 54 of the plate such that the tabs 44, 46 extend beyond the 'watershed' inflexion line of the distal radius bone when the plate is properly positioned on the bone in order to provide a support to the volar fragment, and particularly the ulnar facet 110 thereof (FIGS. 4 and 5). This allows the tabs 44, 46 to claw or buttress the volar fragment. In a preferred embodiment, the tabs 44, 46 may be considered to be located as an ulnar side tab 44 and an intermediate columnar tab 46, with 'intermediate' defining a central location between the ulnar and radial sides of the distal radius when the plate is positioned on the volar side of the distal radius (and not a relative location between other tabs). The ulnar side tab 44 is located distally in front of the medialmost (ulnar side) threaded hole 28a of the distal row 32 of threaded holes 28, and the intermediate tab 46 is located distally and centrally in front of a centrally positioned threaded hole 28b of the distal row 32 of threaded holes 28 (FIG. 1). The tabs 44, 46 each have a smoothly contoured and chamfered upper surface which tapers toward the medial side of the relatively ulnar side tab 44 and toward the lateral side of the intermediate tab 46. This provides the upper surface of the tabs 44, 46 with an atraumatic soft tissue contacting surface that minimizes soft tissue irritation. Referring specifically to FIG. 2, the lower surfaces 62 of the tabs are angled relative to the lower surface 60 at the remainder of the lower surface of the head 14. That is, while the remainder of the lower surface 60 of the head 14 is configured to seat in the concavity on the bone below the 'watershed' inflexion line of the distal radius, the tabs 44, 46 are configured to extend over the watershed line and generally parallel to the volar rim 110. Thus, the lower surfaces 62 of the tabs 44, 46 extend out of orientation with the lower surface 60 of the remainder of the head by an acute angle shown at A. Angle A is preferably between 26° and 30°.

Referring to FIGS. 2 and 3, in accord with the invention, the tabs 44, 46 can be readily re-orientated in situ to better approximate the volar rim 110, and preferably contact a fragment of the volar rim. Each tab 44, 46 is provided with a single K-wire hole 56, 58 each defined by a cylindrical sidewall and specifically sized to closely receive a 1.6 mm K-wire in a fixed angle orientation. A fixed angle orientation is one in which the K-wire is retained coaxial with or within 5°, and more preferably within 3°, of the axis of the K-wire hole. With too much play between the K-wire and plate, the K-wire cannot positively engage the hole to provide accurate bending of the tabs in accord with the desired operation of the system. With respect to K-wire hole 58, the hole has an approximate diameter of 1.6 mm to provide the necessary clearance for passage of the K-wire. The axes of the holes 56, 58 in the tabs 44, 46 are oblique relative to the lower surface 16 at the tabs, as shown by angle β (FIG. 2) and also seen in FIG. 3. The tabs 44, 46 are provided with respective lower recesses 50, 52 preferably formed as an undercut at the junction of the tabs and the remainder of the head of the plate; i.e., in a preferred embodiment, from the lower surface 16 of the plate, the recesses 50, 52 and distal edge 54 of the radial side 40 of the plate are in alignment. The recesses 50, 52 reduce the cross-sectional area moment of inertia at the junction between the tabs 44, 46 and the remainder of the head 14. As a result of the reduced cross-sectional area moment of inertia at the junctions, when a force is applied to a tab, all plastic deformation will be located at the reduced cross-sectional area—leaving the tab and the K-wire hole without deformation—and the tabs 44, 46 will be re-oriented about an axis in alignment with the radial side distal edge 54. The recesses 50, 52 allow each tab 44, 46 to be contoured independently of the other to fit the patient anatomy. Referring to FIGS. 5-8, with the K-wire 200 inserted into the K-wire hole 58 of tab 46, the K-wire 200 is able to apply a bending load to the tab 46 in situ to bend the tab about its lower recess 52, e.g., in the direction of arrow 202, into a new orientation to best match, and preferably contact, the patient anatomy and provide support for the ulnar facet of the volar rim 110. Therefore, the plate does not require a dedicated bender. Moreover, the K-wire 200 is an extremely unobtrusive tool for use during the surgical procedure, providing excellent visibility to the remainder of the plate 10 and surgical wound during the bending operation to allow the surgeon to visually confirm plate-to-anatomy conformation. Using the K-wire 200, the tabs 44, 46 can be bent independently, quickly, and accurately to fit the anatomy. Referring to FIG. 6, it is preferable that, for purposes of tab bending, a K-wire 200 be inserted blunt side 204 down toward the bone to prevent the sharpened tips 206 at the opposite end from catching the bone and inhibiting bending or inadvertently displacing loose bone fragments.

In addition, the K-wire holes 56, 58 can be used for stable, temporary fixation of a volar rim fragment relative to the plate 10 and the remainder of the distal radius 100 with a K-wire. In such use, one or more K-wires are preferably inserted via a drill, with the sharpened side 206 of the K-wire inserted down into the bone.

Turning now to FIG. 10, according to an aspect of the system, a soft tissue anchor 210 is provided that can be used to join soft tissue relative to the tabs 44, 46 and particularly the holes 56, 58 in the tabs of the plate. The soft tissue anchor 210 is provided at the distal end of a rigid deployment shaft 220 having a proximal handle 222. The soft tissue anchor 210 has a first portion 212 that is adapted to engage within a hole in bone when it is deployed into the bone, and a second suture portion 214a, 214b. In one embodiment, the first portion 212 includes a portion of braided fabric cable that can be reconfigured, e.g., by stretching or other longitudinal restraint, from a smaller diameter first configuration during deployment into the drilled hole, to a relatively larger diameter second configuration, e.g., by moving or releasing the ends of the first portion to move towards each other, in which the first portion is adapted to be captured within the drilled hole. The second suture portion includes at least one length of suture 214a extending from the first portion 212, and preferably a second length of suture 214b also extending from the first portion. Each length of suture 214a, 214b is preferably provided with a suture needle 216a, 216b at its end. The needles 216a, 216b can be pierced through soft tissue 218 to draw the lengths of suture through the soft tissue (FIG. 11). The first portion 212 of the soft tissue anchor 210 is specifically sized and adapted to pass directly through the individual holes 56, 58 in the tabs 44, 46 and into the underlying bone to anchor the soft tissue anchor 210 thereat, whereas the second suture portions 214a, 214b are adapted to engage capsular tissue 218 and pull and retain such tissue relative to the plate 10 and bone 110. One preferred soft tissue anchor 210 suitable for use in accord with the system is the JuggerKnot™ soft tissue anchor available from Biomet, Warsaw, Ind., which is described in detail in U.S. Pat. No. 8,562,647, which is hereby incorporated by reference herein.

In use, the plate is positioned on the bone with the primary terminating edge (exclusive of the tabs) located below the boney crest inflexion line on the bone, and with the tabs extending beyond the inflexion line to provide buttress support for bone fragments, e.g., 112. For a distal radius plate, the primary terminating edge seats just below the so-called watershed line 108, whereas the tabs 44, 46 extend beyond the watershed line (FIG. 6). Fixation is provided between the plate and the diaphyseal portion of the bone by inserting fasteners (not shown) through the screw holes 20, 22, 24, 28 in the shaft and head of the plate and into the underlying bone. Referring to FIGS. 7 and 8, to the extent necessary or desired, the tabs are bent, using K-wire 200 or similar device, along the recesses 52 so that the tabs approximate, and more preferably intimately contact the bone, and particularly provide support for boney fragments 112. Turning to FIG. 9, a hole 120 is drilled through a hole 58 in at least one of the tabs 46 and into the underlying the bone or boney fragment.

Using the deployment shaft 220 and operable handle 222, the first portion 212 of the soft tissue anchor 210 is inserted through the hole 58 in one of the tabs 46 and into the drilled hole 120 in the underlying bone and released from the shaft 220. The needles 216a, 216b at the second suture portion 214a, 214b are then pierced through the capsular tissue 218 and the suture is then pulled and manipulated to draw the capsular tissue up to the tab 46 and to thereby close the joint capsule. Such tissue may include the short radiolunate ligament. The suture is then tied off or otherwise secured. A similar procedure may be carried out for tab 44.

Thus, the system and method permit sutures to be applied after the plate has been fully installed, even when the plate is in contact with the underlying bone. This makes the process intuitive, allowing the surgeon to focus on reducing the fracture and correctly securing the plate to the bone prior to addressing the stability of soft tissue. In addition, the system and procedure allow the plate to secured in close intimate contact with the bone, and thus a more stable positioning relative to the bone.

There have been described and illustrated herein embodiments of a volar distal plate. While particular embodiments of the invention have been described, it is not intended that the invention be limited thereto, as it is intended that the invention be as broad in scope as the art will allow and that the specification be read likewise. That is, while an embodiment with a specified number of threaded holes in the plate is described, it is appreciated that a greater or fewer number of threaded holes can be provided in the head of the plate. By way of example, the distal row of threaded holes can include at most two threaded holes. In addition, while the plate is described as having two tabs, it will be appreciated that another number of tabs may be provided to the plate. For example, a single tab may be provided to the ulnar side of the head of the plate. It will therefore be appreciated by those skilled in the art that yet other modifications could be made to the provided invention without deviating from its spirit and scope as claimed.

What is claimed is:

1. A method for stabilizing a fracture of a bone, the bone including a diaphyseal portion and a metaphyseal portion and including a concave articular surface at the end of the metaphyseal portion and a rim extending at least partially about the articular surface, the method comprising:
   a) providing a bone plate including a bone contacting first surface, an opposite second surface, a shaft portion defining a longitudinal axis and including a plurality of fastener holes to receive fasteners to secure the shaft portion relative to the diaphyseal portion of the bone, and an anchor hole extending between the first and second surfaces of the plate;
   b) positioning the plate on the bone;
   c) drilling through the anchor hole and into the underlying bone to form a bore in the bone;
   d) providing a soft tissue anchor including a bone engaging first portion and flexible suture second portion;
   e) inserting the first portion of the soft tissue anchor through the anchor hole and engaging the first portion within the bore in the bone;
   f) passing the second portion through soft tissue; and
   g) retaining the soft tissue relative to the plate with the second portion of the tissue anchor.

2. The method according to claim 1, wherein the bone plate further includes a head portion angled relative to the shaft portion, such that the head portion is configured to be secured relative to the metaphyseal portion of the bone.

3. The method according to claim 2, wherein the head portion includes a reorientable tab unitary with the head portion.

4. The method according to claim 3, wherein the reorientable tab defines a hole extending between the first and second surfaces of the plate.

5. The method according to claim 1, further comprising: drawing the soft tissue toward the reorientable tab.

6. A method for stabilizing a fracture of a bone, the bone including a diaphyseal portion and a metaphyseal portion and including a concave articular surface at the end of the metaphyseal portion and a rim extending at least partially about the articular surface, the method comprising:
   a) providing a bone plate including a bone contacting first surface, an opposite second surface, a shaft portion defining a longitudinal axis and including a plurality of fastener holes to secure the shaft portion relative to the diaphyseal portion of the bone, and a head portion angled relative to the shaft portion to secure the head portion relative to the metaphyseal portion of the bone, the head portion including a reorientable tab unitary with the head portion, the tab including a hole extending between the first and second surfaces of the plate;
   b) positioning the plate on the bone such that first surface of the head portion to one side of the tab seats proximally below the rim of the metaphyseal portion, and the tab extends over the rim of the metaphyseal portion;
   c) reorienting the tab to more closely approximate the rim;
   d) drilling through the hole in the tab and into the underlying bone to form a bore in the bone;
   e) providing a soft tissue anchor including a bone engaging first portion and a flexible suture second portion;
   f) inserting the first portion of the soft tissue anchor through the hole in the tab and engaging the first portion within the bore in the bone; and
   g) passing the second portion through soft tissue.

7. The method according to claim 6, further comprising drawing the soft tissue toward the tab.

8. The method according to claim 7, wherein the soft tissue is joint capsular tissue.

9. The method according to claim 6, wherein the second portion of the soft tissue anchor has an end provided with a suture needle.

10. The method according to claim 6, wherein the second portion includes two separate lengths of flexible suture material, each including an end provided with a suture needle.

11. The method according to claim 6, wherein the reorienting the tab positions the tab in contact with the bone.

12. The method according to claim 6, wherein the head of the bone plate includes a first side and an opposing second side and a plurality of fastener holes provided therein adapted to receive fasteners therethrough, the second side of the head portion is provided with the tab, and the first side is absent of a tab.

13. The method according to claim 12, wherein the head of the bone plate includes an intermediate portion between the first and second sides, the intermediate portion provided with a second reorientable tab unitary with the head portion, the second tab including a hole extending between the first and second surfaces of the plate.

14. The method according to claim 6, wherein the bone is a distal radius bone, and the rim is the volar rim.

15. A method for stabilizing a fracture of a bone, the bone including a diaphyseal portion and a metaphyseal portion and including a concave articular surface at the end of the metaphyseal portion and a rim extending at least partially about the articular surface, the method comprising:
   providing a bone plate including a bone contacting first surface, an opposite second surface, a shaft portion defining a longitudinal axis and including a plurality of fastener holes to secure the shaft portion relative to the diaphyseal portion of the bone, and a head portion angled relative to the shaft portion to secure the head portion relative to the metaphyseal portion of the bone, the head portion including a reorientable tab unitary with the head portion, the tab including a hole extending between the first and second surfaces of the plate;
   positioning the plate on the bone such that first surface of the head portion to one side of the tab seats proximally below the rim of the metaphyseal portion, and the tab extends over the rim of the metaphyseal portion;
   drilling through the hole in the tab and into the underlying bone to form a bore in the bone;
   inserting a soft tissue anchor into the bore to engage bone; and
   coupling the soft tissue anchor to soft tissue.

16. The method according to claim 15, wherein:
   the soft tissue anchor includes a bone engaging first portion and a flexible suture second portion.

17. The method according to claim 16, wherein inserting the soft tissue anchor into the bone comprises inserting the bone engaging first portion of the soft tissue anchor through the hole in the tab and into the bore.

18. The method according to claim 17, wherein coupling the soft tissue anchor to soft tissue comprises passing the flexible suture second portion through soft tissue.

19. The method according to claim 16, wherein the flexible suture second portion includes a suture needle for engaging soft tissue.

20. The method according to claim 15 further comprising:
   reorienting the tab to more closely approximate the rim prior to drilling through the hole in the tab.

* * * * *